(12) United States Patent
Motley et al.

(10) Patent No.: US 6,613,341 B2
(45) Date of Patent: Sep. 2, 2003

(54) TOPICAL COMPOSITION COMPRISING A SUBSTITUTED COSMETIC BONDING AGENT

(75) Inventors: Curtis Bobby Motley, West Chester, OH (US); Christopher Todd Morrissey, Mason, OH (US); Haimanot Bekele, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/158,506

(22) Filed: May 30, 2002

(65) Prior Publication Data

US 2003/0044437 A1 Mar. 6, 2003

Related U.S. Application Data

(60) Provisional application No. 60/294,275, filed on May 30, 2001.

(51) Int. Cl.[7] ............... A61K 7/00; A61K 7/04; A61K 7/027; A61K 7/42; A61K 31/695
(52) U.S. Cl. ............ 424/401; 424/47; 424/59; 424/61; 424/63; 424/64; 514/63
(58) Field of Search ............... 424/47, 59, 61, 424/63, 64; 514/63

(56) References Cited

U.S. PATENT DOCUMENTS

| | | |
|---|---|---|
| 3,396,736 A | 8/1968 | Shansky |
| 4,004,074 A | 1/1977 | Gerecht et al. |
| 4,560,555 A | 12/1985 | Snider |
| 4,572,831 A | 2/1986 | Rosen |
| 5,047,249 A | 9/1991 | Rothman et al. |
| 5,211,942 A | 5/1993 | Deppert et al. |
| 5,490,980 A | 2/1996 | Richardson et al. |
| 5,523,080 A | 6/1996 | Gough et al. |
| 5,525,332 A | 6/1996 | Gough et al. |
| 5,525,336 A | 6/1996 | Green et al. |
| 5,877,204 A | 3/1999 | Davison et al. |

FOREIGN PATENT DOCUMENTS

| | | |
|---|---|---|
| DE | 198 42 069 A | 3/2000 |
| EP | 0 615 745 B1 | 5/1997 |
| EP | 0 758 314 B1 | 9/1999 |
| EP | 1 172411 A1 | 1/2002 |
| JP | 2000 319134 A | 11/2000 |
| JP | 2000 226763 A | 1/2001 |
| JP | 2001 011068 A | 1/2001 |
| WO | WO 94/18945 A1 | 9/1994 |
| WO | WO 94/26237 A1 | 11/1994 |
| WO | WO 95/30646 A1 | 11/1995 |
| WO | WO 96/40791 | 12/1996 |
| WO | WO 97/30688 | 8/1997 |
| WO | WO 98/38974 A1 | 9/1998 |
| WO | WO 99/29294 A1 | 6/1999 |
| WO | WO 00/00163 A1 | 1/2000 |
| WO | WO 00/15036 A1 | 3/2000 |
| WO | WO 00/59458 A1 | 10/2000 |
| WO | WO 01/06829 A2 | 2/2001 |
| WO | WO 01/07009 A | 2/2001 |

OTHER PUBLICATIONS

McBroom, C.R., "Carbohydrate Antigens: Coupling of Carbohydrates to Proteins by Diazonium and Phenylisothiocyanate Reactions", Methods in Enzymology—IIVIII—Complex Carbohydrates—Part B—Ed. Ginsburg, V., pp. 212–222 (1972).

*Primary Examiner*—Shelley A. Dodson
(74) *Attorney, Agent, or Firm*—Dara M. Kendall; Tara M. Rosnell; Karen F. Clark

(57) ABSTRACT

The present invention relates to cosmetic compositions that comprise a safe and effective amount of a bonding agent comprising the structure

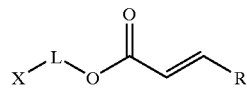

wherein X represents a cosmetic benefit agent; L represents an optional chemical linker; and R represents a hydrocarbon chain that optionally contains heteroatoms; and a cosmetically acceptable carrier for the bonding agent wherein the composition is administered topically to a mammalian proteinaceous substrate and wherein the bonding agent reacts with a protein contained in the substrate such that the bonding agent is covalently attached to the substrate. The invention further relates to methods of using the compositions described above as well as various products that include the claimed compositions.

15 Claims, No Drawings

TOPICAL COMPOSITION COMPRISING A SUBSTITUTED COSMETIC BONDING AGENT

CROSS REFERENCE TO RELATED APPLICATION

This application claims the benefit of U.S. Provisional Application No. 60/294,275, filed May 30, 2001.

FIELD OF INVENTION

The present invention relates to cosmetic compositions suitable for use on mammalian skin. These compositions comprise a bonding agent capable of attaching a cosmetic benefit agent to mammalian skin. In particular, the bonding agent is linked to the cosmetic benefit agents that are then in turn linked directly or indirectly to the skin.

BACKGROUND

It is well known in the skin beauty care field that cosmetic benefit agents may be topically applied to human skin. There are a number of benefit agents that can be applied to the skin for varying purposes including moisturizers, humectants, color cosmetics, etc. There is, however, a common problem that arises in each of these areas of beauty care. The problem is the failure of the above-mentioned cosmetic benefit agents to remain substantively attached to the skin to which they are applied. That is, the benefit agents that are applied fail to "stick" to the skin such that a long-wear result is achieved to any noticeable extent.

The present invention seeks to solve this substantivity deficiency that is typical in topically applied products by utilizing a chemical hook based technology. The operative chemical hook of the present invention is a bonding agent that serves as a gluing mechanism between a cosmetic benefit agent of interest and one or more protein molecules that are found in the skin and/or hair. In particular, Applicants have found that activating certain molecules then allows them to serve as suitable bonding agents such that improved substantivity of various benefit agents are observed on the skin. Additionally, Applicants have found that, due to the selective reactivity of the bonding agents with the proteins in the skin, an unexpected evenness of coverage benefit is also imparted by the use of the claimed compositions. That is, undesirable caking or build-up of a benefit agent does not result since substantivity only occurs at the reactive sites between the bonding agents and proteins found in the substrate.

Without being limited by theory, the chemical hook bonding agents covalently bond to certain amino acids present in proteinaceous substrates like skin, cuticles, and hair to form a substantive attachment of the desired cosmetic benefit agent to the substrate as demonstrated by the chemical reaction that follows

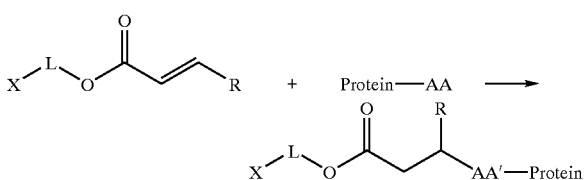

wherein AA represents functional amino acids containing amino, sulfhydryl, carboxyl, or hydroxyl groups and wherein X, L, and R are defined below.

SUMMARY OF THE INVENTION

The present invention relates to cosmetic compositions that comprise a safe and effective amount of a bonding agent comprising structure

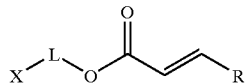

wherein X represents a cosmetic benefit agent; L represents an optional chemical linker between X and the remainder of the bonding agent; and R represents a hydrocarbon chain that optionally contains heteroatoms; and a cosmetically acceptable carrier for the bonding agent wherein the composition is administered topically to a mammalian proteinaceous substrate and wherein the bonding agent reacts with a protein contained in the substrate such that the bonding agent is covalently attached to the substrate, in particular, proteins and other reactive components of the skin. The invention further relates to methods of using the compositions described above as well as various products that include the claimed compositions.

DETAILED DESCRIPTION OF THE INVENTION

The present invention relates to topical compositions capable of delivering substantively attached cosmetic benefit agents to mammalian skin. The essential components of these compositions are described below. Also included is a nonexclusive description of various optional and preferred components useful in embodiments of the present invention.

As used herein, "safe and effective amount" means an amount of a compound, component, or composition (as applicable) sufficient to significantly induce a positive effect (e.g., confer a noticeable cosmetic benefit), but low enough to avoid serious side effects, (e.g., undue toxicity or allergic reaction), i.e., to provide a reasonable benefit to risk ratio, within the scope of sound medical judgment.

As used herein, "cosmetic benefit agent" means a compound, material, and/or active that confers an aesthetic feature to the substrate to which it is applied, which is preferably skin.

As used herein, "chemical linker" refers to a hydrocarbon chain, optionally containing heteroatoms, e.g., S, N, Se, O, substituted or unsubstituted aryls, Si, SiO, siloxane "D" groups [{(CH$_3$)}—Si—O$_3$], siloxane "M" groups [{(CH$_3$)$_3$}—Si—O], siloxane "T" groups [{(CH$_3$)}—Si—O$_{3/2}$], esters thiol esters, amides, and selenium esters, that form a covalent bond between the cosmetic benefit agent and the bonding agent such that a "chemical hook" is formed.

The present invention can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All molar weights are weight average molecular weights and are given in units of grams per mole.

All ingredient levels are exclusive of solvents, by-products, or other impurities that may be present in commercially available sources, unless otherwise indicated.

All measurements made are at ambient room temperature, which is approximately 73° F., unless otherwise designated.

All documents referred to herein, including patents, patent applications, and printed publications, are hereby incorporated by reference in their entirety in this disclosure.

Bonding Agent

The compositions of the present invention comprise a bonding agent comprising structure

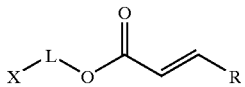

wherein X represents a cosmetic benefit agent; L represents an optional chemical linker between X and the remainder of the bonding agent; and R represents a hydrocarbon chain that optionally contains heteroatoms.

A particular embodiment of the present invention includes a composition comprising a bonding agent comprising the following structure

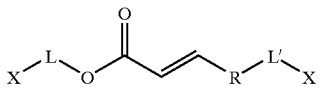

wherein X represents a cosmetic benefit agent, L and L' represent optional chemical linkers between X and a remainder of the bonding agent; and R represents a hydrocarbon chain that optionally contains heteroatoms. In each of these embodiments, it is conceivable that multiple chemical hook entities may extend from one or more of the cosmetic benefit agents that are contained in the core of the bonding agent. Moreover, multiple cosmetic benefit agents may be attached to the bonding agent of the present invention. For instance, a bonding agent may be attached to or include a vitamin, a sunscreen active, an antioxidant, and others, in combination.

More preferably, R is an alkyl selected from the group consisting of a methyl, ethyl, propyl, butyl, and combinations thereof.

Suitable chemical linkers, L and L', include, but are not limited to, hydrocarbon chains containing heteroatoms like S, N, Se, O, substituted or unsubstituted aryls, Si, SiO, siloxane "D" groups [{(CH$_3$)}—Si—O$_3$], siloxane "M" groups [{(CH$_3$)$_3$}—Si—O], siloxane "T" groups [{(CH$_3$)}—Si—O$_{3/2}$], etc.

Without being limited by theory, Applicant believes that the bonding agent may exist in trans or cis conformation but that trans is preferred.

The cosmetic benefit agent of the present invention is suitable for providing therapeutic or aesthetic skin benefits by deposition and consequent adhesion to skin. Suitable cosmetic agents include, but are not limited to those selected from the group consisting of absorbents, anti-acne actives, anti-caking agents, anti-cellulite agents, anti-foaming agents, anti-fungal actives, anti-inflammatory actives, anti-microbial actives, anti-oxidants, antiperspirant/deodorant actives, anti-skin atrophy actives, anti-viral agents, anti-wrinkle actives, artificial tanning agents and accelerators, astringents, barrier repair agents, binders, buffering agents, bulking agents, chelating agents, colorants, dyes, enzymes, essential oils, film formers, flavors, fragrances, humectants, hydrocolloids, light diffusers, nail enamels, opacifying agents, optical brighteners, optical modifiers, particulates, perfumes, pH adjusters, sequestering agents, skin conditioners/moisturizers, skin feel modifiers, skin protectants, skin sensates, skin treating agents, skin exfoliating agents, skin lightening agents, skin soothing and/or healing agents, skin thickeners, sunscreen actives, topical anesthetics, vitamin compounds, and combinations thereof.

Suitable colorants include those used in foundations, blushes, blemish-covering compositions, and other typical color cosmetic products. Such agents, in effect, result in a cosmetic composition that is suitable for make-up application.

The cosmetic benefit agents of the present invention are well suited and capable of attaching (either removably or fixably) to the bonding agent via the chemical linker. In preferred embodiments, the compositions of the present invention comprise from about 0.001% to about 50%, by weight of the composition, of the bonding agent that includes the cosmetic benefit agent. In fact, even more preferred amounts of the combination in increasing order of preference are from about 0.01% to about 35%, 0.1% to about 20%, 0.1% to about 15%, 1% to about 10%, and 2% to about 7%, by weight of the composition. Furthermore, in such combinations it is preferred that the combination of the bonding agent and cosmetic benefit agent comprise from about 10% to about 90%, by weight of the combination, of the cosmetic benefit agent. More preferably, the combination comprises from about 20% to about 90%, of the cosmetic benefit agent. Even more preferably, the combination comprises from about 30% to 85%, of the cosmetic benefit agent. Still more preferably, the combination comprises about 50% of the cosmetic benefit agent. Suitable cosmetic benefit agents include but are not limited to those that follow.

Hydrophobic Conditioning Agents

The cosmetic benefit agent may be one or more hydrophobic conditioning agents. Preferably, the weighted arithmetic mean solubility parameter of the hydrophobic conditioning agent is less than or equal to 12. It is recognized, based on this mathematical definition of solubility parameters, that it is possible, for example, to achieve the required weighted arithmetic mean solubility parameter, i.e., less than or equal to 12, for a hydrophobic conditioning agent comprising two or more compounds if one of the compounds has an individual solubility parameter greater than 12.

The solubility parameter of a chemical compound, δ, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[\frac{\sum_i E_i}{\sum_i m_i}\right]^{1/2}$$

wherein $\Sigma_i E_i$=the sum of the heat of vaporization additive group contributions, and $\Sigma_i m_i$=the sum of the molar volume additive group contributions Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974).

Solubility parameters obey the law of mixtures such that the solubility parameter for a mixture of materials is given by the weighted arithmetic mean (i.e., the weighted average) of the solubility parameters for each component of that mixture. See, *Handbook of Chemistry and Physics*, 57th edition, CRC Press, p. C-726 (1976–1977.

Solubility parameters have also been tabulated for a wide variety of chemical materials. Tabulations of solubility parameters are found in the above-cited *Handbook of Solubility Parameters*. Also, see "Solubility Effects In Product, Package, Penetration, And Preservation", C. D. Vaughan, *Cosmetics and Toiletries*, vol. 103, October 1988, pp. 47–69.

Nonlimiting examples of hydrophobic conditioning agents include those selected from the group consisting of mineral oil, petrolatum, lecithin, hydrogenated lecithin, lanolin, lanolin derivatives, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and combinations thereof.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e., a $C_{22}$ hydrocarbon), hexadecane, isohexadecane (a commercially available hydrocarbon sold as Permethyl® 101A by Presperse, South Plainfield, N.J.). C7–C40 isoparaffins, a class of C7–C40 branched hydrocarbons, are useful herein. Polydecene, a branched liquid hydrocarbon, is also useful herein and is commercially available under the tradenames Puresyn 100® and Puresyn 3000® from Mobile Chemical (Edison, N.J.).

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, carpylic/capric triglyceride, PEG-6 caprylic/capric triglyceride, PEG-8 caprylic/capric triglyceride, and combinations thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates: behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably, R is methyl or ethyl, more preferably methyl)

and x is an integer up to about 500, chosen to achieve the desired molecular weight. Commercially available dimethiconols are typically sold as mixtures with dimethicone or cyclomethicone (e.g., Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl modified siloxanes such as alkyl methicones and alkyl dimethicones wherein the alkyl chain contains 10 to 50 carbons. Such siloxanes are commercially available under the tradenames ABIL WAX 9810® ($C_{24}$–$C_{28}$ alkyl methicone) (sold by Goldschmidt) and SF1632 (cetearyl methicone)(sold by General Electric Company). Cyclomethicone/dimethicone copolyol mixtures are also particularly useful as formulation aid/conditioning agents. A suitable mixture is sold under the tradename DC 3225Q®.

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Hydrophobic chelating agents are also useful herein as hydrophobic conditioning agents. Suitable agents are described in U.S. Pat. No. 4,387,244, issued to Scanlon et al. on Jun. 7, 1983, and U.S. patent application Ser. Nos. 09/258,747 (published as WO 99/52502 on Oct. 21, 1999) and 09/259,485 (published as WO 99/52501 on Oct. 21, 1999), filed in the names of Schwartz et al. on Feb. 26, 1999.

Preferred hydrophobic conditioning agents are selected from the group consisting of mineral oil, petrolatum, lecithin, hydrogenated lecithin, lanolin, lanolin derivatives, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkylarylsiloxanes, cylcomethicones having 3 to 9 silicon atoms, vegetable oils, hydrogenated vegetable oils, polypropylene glycol C4–C20 alkyl ethers, di C8–C30 alkyl ethers, and combinations thereof.

Hydrophilic Conditioning Agents

The cosmetic benefit agents of the present invention can also be one or more hydrophilic conditioning agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the articles of the present invention. Also useful are materials such as aloe vera in any of its variety of forms (e.g., aloe vera gel), chitosan and chitosan derivatives, e.g., chitosan lactate, lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990.

Structured Conditioning Agents

The cosmetic benefit agents of the present invention may also be structured conditioning agents. Suitable structured conditioning agents include, but are not limited to, vesicular structures such as ceramides, liposomes, and the like.

Coacervates

The cosmetic benefit agents of the present invention can be coacervate-forming. Preferably, the coacervate-forming cosmetic benefit agent comprises a cationic polymer, an anionic surfactant, and a dermatologically acceptable carrier for the polymer and surfactant. The cationic polymer may be selected from the group consisting of natural backbone quaternary ammonium polymers, synthetic backbone quaternary ammonium polymers, natural backbone amphoteric type polymers, synthetic backbone amphoteric type polymers, and combinations thereof.

More preferably, the cationic polymer is selected from the group consisting of natural backbone quaternary ammonium polymers selected from the group consisting of Polyquaternium-4, Polyquaternium-10, Polyquaternium-24, PG-hydroxyethylcellulose alkyldimonium chlorides, guar hydroxypropyltrimonium chloride, hydroxypropylguar hydroxypropyltrimonium chloride, and combinations thereof; synthetic backbone quaternary ammonium polymers selected from the group consisting of Polyquaternium-2, Polyquaternium-6, Polyquaternium-7, Polyquaternium-11, Polyquaternium-16, Polyquaternium-17, Polyquaternium-18, Polyquaternium-28, Polyquaternium-32, Polyquaternium-37, Polyquaternium-43, Polyquaternium-44, Polyquaternium-46, polymethacylamidopropyl trimonium chloride, acrylamidopropyl trimonium chloride/acrylamide copolymer, and combinations thereof; natural backbone amphoteric type polymers selected from the group consisting of chitosan, quaternized proteins, hydrolyzed proteins, and combinations thereof; synthetic backbone amphoteric type polymers selected from the group consisting of Polyquaternium-22, Polyquaternium-39, Polyquaternium-47, adipic acid/dimethylaminohydroxypropyl diethylenetriamine copolymer, polyvinylpyrrolidone/dimethylyaminoethyl methacyrlate copolymer, vinylcaprolactam/polyvinylpyrrolidone/dimethylaminoethylmethacrylate copolymer, vinaylcaprolactam/polyvinylpyrrolidone/dimethylaminopropylmethacrylamide terpolymer, polyvinylpyrrolidone/dimethylaminopropylmethacrylamide copolymer, polyamine, and combinations thereof; and combinations thereof. Even more preferably, the cationic polymer is a synthetic backbone amphoteric type polymer. Even still more preferably, the cationic polymer is a polyamine.

When the cationic polymer is a polyamine, it is preferred that the cationic polyamine polymer be selected from the group consisting of polyethyleneimines, polyvinylamines, polypropyleneimines, polylysines and combinations thereof. Even more preferably, the cationic polyamine polymer is a polyethyleneimine.

In certain embodiments in which the cationic polymer is a polyamine, the polyamine may be hydrophobically or hydrophilically modified. In this instance, the cationic polyamine polymer is selected from the group consisting of benzylated polyamines, ethoxylated polyamines, propoxylated polyamines, alkylated polyamines, amidated polyamines, esterified polyamines and combinations thereof. The composition comprises from about 0.01% to about 20%, more preferably from about 0.05% to about 10%, and most preferably from about 0.1% to about 5%, by weight of the composition, of the cationic polymer.

Preferably, for the coacervate-forming cosmetic benefit agent, the anionic surfactant is selected from the group consisting of sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isethionates, glycerylether sulfonates, sulfosuccinates and combinations thereof. More preferably, the anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

Suitable coacervate-forming agents are further described in U.S. patent application Ser. Nos. 09/397,747, filed in the name of Schwartz et al.; No. 09/397,746, filed in the name of Heinrich et al.; No. 09/397,712, filed in the name of Schwartz et al.; 09/397,723, filed in the name of Heinrich et al.; and 09/397,722, filed in the name of Venkitaraman et al.; each of which were filed on Sep. 16, 1999.

Alternatively, the coacervate-forming cosmetic benefit agent may comprise an anionic polymer, a cationic surfactant, and a dermatologically acceptable carrier for the polymer and surfactant. The anionic polymer may be selected from the group consisting of polyacrylic acid polymers, polyacrylamide polymers, copolymers of acrylic acid, acrylamide, and other natural or synthetic polymers (e.g., polystyrene, polybutene, polyurethane, etc.), naturally derived gums, and combinations thereof. Suitable gums include alginates (e.g., propylene glycol alginate), pectins, chitosans (e.g., chitosan lactate), and modified gums (e.g., starch octenyl succinate), and combinations thereof. More preferably, the anionic polymer is selected from the group consisting of polyacrylic acid polymers, polyacrylamide polymers, pectins, chitosans, and combinations thereof.

Suitable cationic surfactants include, but are not limited to, those discussed herein.

Colorants

The present compositions may comprise a bonding agent that comprises one or more colorants. Suitable colorants include, but are not limited to, pigments, dyes or lakes or a combination thereof as the cosmetic benefit agents. Preferred pigments include, but are not limited to, iron oxides, and titanium oxides. Suitable dyes include FD&C approved colorants, D&C approved colorants, and those approved for use in Europe and Japan. See, Marmion, D. M., *Handbook of US Colorants for Food, Drugs, Cosmetics, and Medical Devices,* 3rd ed, 1991.

Vitamin Compounds

The present compositions may comprise vitamin compounds, precursors, and derivatives thereof as the cosmetic benefit agents. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

For instance, vitamin $B_3$ compounds are particularly useful for regulating skin condition as described in U.S. Pat. No. 5,939,082 issued Aug. 17, 1999 in the names of Oblong et al. The compositions of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

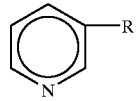

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

Anti-Acne Actives

Examples of useful anti-acne actives as the cosmetic benefit agents of the present invention include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives

Examples of anti-wrinkle and anti-skin atrophy actives useful as the cosmetic benefit agents of the present invention include, but are not limited to, bisabolol, phytantriol, retinoic acid and its derivatives (e.g., cis and trans); retinol; retinyl esters; niacinamide, and derivatives thereof; sulfur-containing D and L amino acids and their derivatives and salts, particularly the N-acetyl derivatives, a preferred example of which is N-acetyl-L-cysteine; thiols, e.g., ethane thiol; terpene alcohols (e.g., farnesol); hydroxy acids, phytic acid, lipoic acid; lysophosphatidic acid, alpha-hydroxy acids (e.g., lactic acid and glycolic acid), beta-hydroxy acids (e.g., salicylic acid), and skin peel agents (e.g., phenol and the like). Combinations of these actives are also suitable for inclusion into the compositions of the present invention. Such combinations are further described in the copending U.S. patent applications having the following Ser. Nos. 09/544,788, 09/544,783; 09/544,790; and 09/544,791; each filed on Apr. 7, 2000.

Enzymes

The cosmetic benefit agents of the present invention may be one or more enzymes. Preferably, such enzymes are dermatologically acceptable. Suitable enzymes include, but are not limited to, keratinase, protease, amylase, subtilisin, other peptides and proteins, etc.

Peptides, including but not limited to, di-, tri-, tetra-, and pentapeptides and derivatives thereof, may be included as the cosmetic benefit agents of the present invention in amounts that are safe and effective. As used herein, "peptides" refers to both the naturally occuring peptides and synthesized peptides. Also useful herein are naturally occurring and commercially available compositions that contain peptides. For instance, Matrixyl® is a commercially available pentapeptide derivative that is suitable for inclusion in the compositions of the present invention when being used to regulate the condition of mammalian skin as detailed in copending U.S. patent application Ser. No. 09/544,789, filed on Apr. 7, 2000.

Sunscreen Actives

Also useful herein as cosmetic benefit agents are sunscreen actives. A wide variety of sunscreening actives are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Sagarin, et al., at Chapter VIII, pages 189 et seq., of *Cosmetics Science and Technology*. Nonlimiting examples of sunscreen actives that are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyidibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreen actives that can be employed will vary depending upon the sunscreen chosen and the desired Sun Protection Factor (SPF) to be achieved. SPF is a commonly used measure of photoprotection of a sunscreen against erythema.

Chelators

The bonding agents of the present compositions may also include chelators as the cosmetic benefit agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the compositions of the subject invention, preferably in amounts of from about 0.1% to about 10%, more preferably from about 1% to about 5%, by weight of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime, furildioxime derivatives, furilmonoxime, furilmonoxime derivatives, and combinations thereof.

Flavonoids

The cosmetic benefit agents of the present invention may also be a flavonoid compound. Flavonoids are broadly disclosed in U.S. Pat. Nos. 5,686,082 and 5,686,367. Flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein relative to flavonoids means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), monohydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. Most preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., a glycoside, an ester or an ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and most preferably from about 0.5% to about 5%.

Sterols

The cosmetic benefit agents of the present invention may also be a safe and effective amount of one or more sterol compounds. Examples of useful sterol compounds include sitosterol, stigmasterol, campesterol, brassicasterol, lanosterol, 7-dehydrocholesterol, and mixtures thereof. These can be synthetic in origin or from natural sources, e.g., blends extracted from plant sources (e.g., phytosterols).

Anti-Cellulite Agents

The cosmetic benefit agent may also be an anti-cellulite agent. Suitable agents may include, but are not limited to, xanthine compounds (e.g., caffeine, theophylline, theobromine, and aminophylline), forskolin, and derivatives thereof.

Skin Lightening Agents

Another suitable cosmetic benefit agent is a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, deoxyarbutin, ascorbic acid and derivatives thereof, e.g., magnesium ascorbyl phosphate or sodium ascorbyl phosphate or other salts of ascorbyl phosphate.

Cosmetically Acceptable Carrier

The compositions of the present invention comprise a cosmetically-acceptable carrier or vehicle for bonding agent and any optional components. Suitable carriers are well known in the art and are selected based on the end use application. For example, carriers of the present invention include, but are not limited to, those suitable for application to skin. Preferably, the carriers of the present invention are suitable for application to skin (e.g., sunscreens, creams, milks, lotions, masks, serums, etc.) and nails (e.g., polishes, treatments, etc.). Such carriers are well-known to one of ordinary skill in the art, and can include one or more compatible liquid or solid filler diluents or vehicles which are suitable for application to skin and nails. The exact amount of carrier will depend upon the level of the bonding agent and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The carrier and compositions herein can be formulated in a number of ways, including but not limited to emulsions (in emulsion technology, a composition comprises a "dispersed phase" and a "continuous phase;" the dispersed phase existing as small particles or droplets that are suspended in and surrounded by a continuous phase). For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The compositions of the present invention can be formulated into a wide variety of product types, including creams, waxes, pastes, lotions, milks, mousses, gels, oils, tonics, and sprays. Preferred compositions are formulated into lotions, creams, gels, and sprays. These product forms may be used for a number of applications, including, but not limited to, hand and body lotions, cold creams, facial moisturizers, anti-acne preparations, topical analgesics, make-ups/cosmetics including foundations, eyeshadows, lipsticks, and the like. Any additional components required to formulate such products vary with product type and can be routinely chosen by one skilled in the art.

If compositions of the present invention are formulated as an aerosol and applied to the skin as a spray-on product, a propellant is added to the composition. Examples of suitable propellants include chlorofluorinated lower molecular weight hydrocarbons. A more complete disclosure of propellants useful herein can be found in Sagarin, *Cosmetics Science and Technology*, 2nd Edition, Vol. 2, pp. 443–465 (1972).

Optional Ingredients

The compositions of the present invention may contain a variety of other components such as are conventionally used in a given product type provided that they do not unacceptably alter the benefits of the invention. These optional components should be suitable for application to mammalian skin, that is, when incorporated into the compositions they are suitable for use in contact with human skin without undue toxicity, incompatibility, instability, allergic response, and the like, within the scope of sound medical or formulator's judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: each agent described as a suitable cosmetic benefit agent for the present invention, enzymes, surfactants, abrasives, skin exfoliating agents, absorbents, aesthetic components such as fragrances, essential oils, skin sensates, astringents, etc. (e.g., clove oil, menthol, camphor, eucalyptus oil, eugenol, menthyl lactate, witch hazel distillate), anti-caking agents, antifoaming agents, antimicrobial agents (e.g., iodopropyl butylcarbamate), binders, biological additives, buffering agents, bulking agents, chemical additives, denaturants, external analgesics, polymer beads, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin soothing and/or healing agents (e.g., panthenol and derivatives (e.g., ethyl panthenol), aloe vera, pantothenic acid and its derivatives, allantoin, bisabolol, and dipotassium glycyrrhizinate), thickeners, hydrocolloids, and particular zeolites. The compositions of the present invention may include carrier components such as are known in the art. Such carriers can include one or more compatible liquid or solid filler diluents or vehicles that are suitable for application to skin.

The optional components useful herein can be categorized by their therapeutic or aesthetic benefit or their postulated mode of action. However, it is to be understood that the optional components useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the cosmetically acceptable salts of the components are useful herein.

Non-Steroidal Anti-inflammatory Actives (NSAIDS)

Examples of NSAIDS useful in the compositions of the present invention include, but are not limited to, the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics

Examples of topical anesthetic drugs suitable for inclusion in the compositions of the present invention include, but are not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Actives and Accelerators

Examples of artificial tanning actives and accelerators useful in the compositions of the present invention include, but are not limited to, dihydroxyacetaone, tyrosine, tyrosine esters such as ethyl tyrosinate, and phospho-DOPA.

Antimicrobial and Antifungal Actives

Examples of antimicrobial and antifungal actives useful in the compositions of the present invention include, but are not limited to, β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

Anti-Viral Agents

The compositions of the present invention may further comprise one or more anti-viral agents. Suitable anti-viral agents include, but are not limited to, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent application Ser. Nos. 09/421,084 (Beerse et al.); 09/421,131 (Biedermann et al.); 09/420,646 (Morgan et al.); and 09/421,179 (Page et al.), which were each filed on Oct. 19, 1999.

Hydrocolloids

Hydrocolloids are well known in the art and are helpful in extending the useful life of the surfactants. Thus, these would be useful for inclusion particularly in those embodiments intended for cleansing the skin, e.g., a showering or bathing experience. Suitable hydrocolloids include, but are not limited to, xanthan gum, carboxymethyl cellulose, hydroxyethyl cellulose, hydroxylpropyl cellulose, methyl and ethyl cellulose, natural gums, gudras guar gum, bean gum, natural starches, deionitized starches (e.g., starch octenyl succinate) and the like.

Oil-soluble Polymeric Gelling Agents

The compositions of the present invention may optionally comprise one or more polymeric materials that are oil-soluble and form a gel with hydrophobic materials (e.g., oils) that are contained in the compositions. Such polymers are beneficial for structuring these materials resulting in flexible gels with improved stability and shear-resistance.

Particularly suitable are at least partially cross-linked oil-soluble polymeric materials with a softening point<160° C. Suitable materials come from the chemical groups of PE (polyethylenes), PVA (polyvinyl alcohols) and derivatives, PVP (polyvinylpyrrolidones) and derivatives, PVP/Alkene Copolymers, PVP/VA copolymers, PVM/MA (methyl vinyl ether/maleic anhydride) copolymers and their esters and ethers, particularly poly (alkyl vinyl ether-co-maleic anhydride) copolymers, ethylene/VA copolymers, styrene/isoprene, styrene/ethylene/butylene, styrene/ethylene/propylene, styrene/ethylene/butylene/styrene and styrene/butadiene copolymers. Suitable materials are available from suppliers like Dupont (ELVAX® types), BASF (LUVISKOL® types), Shell (KRATON® polymers) and ISP (PVP, GANTREZ® and GANEX® types).

Hydrophilic Gelling Agent

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa·s, more preferably at least about 10,000 mPa·s and especially at least 50,000 mPa·s.

Suitable hydrophilic gelling agents can generally be described as water-soluble or colloidally water-soluble polymers, and include cellulose ethers (e.g., hydroxyethyl cellulose, methyl cellulose, hydroxypropylmethyl cellulose), polyvinylpyrrolidone, polyvinylalcohol, polyquaternium-10, guar gum, hydroxypropyl guar gum and xanthan gum.

Among suitable hydrophilic gelling agents are acrylic acid/ethyl acrylate copolymers and the carboxyvinyl polymers sold by the B. F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934®, Carbopol 940®, Carbopol 950®, Carbopol 980®, Carbopol 951®) and Carbopol 981®. Carbopol 934®) is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382®, Carbopol 1342® and Pemulen TR-1® (CTFA Designation: Acrylates/10–30 Alkyl Acrylate Crosspolymer). A combination of the polyalkenyl polyether cross-linked acrylic acid polymer and the hydrophobically modified cross-linked acrylic acid polymer is also suitable for use herein. Other suitable gelling agents suitable for use herein are oleogels such as trihydroxystearin and aluminium magnesium hydroxy stearate. The gelling agents herein are particularly valuable for providing excellent stability characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

Surfactants

Surfactants can also be included into the compositions of the present invention, particularly when the compositions are useful for cleansing skin. A lathering surfactant is preferred for use in such instances. As used herein, "lathering surfactant" means a surfactant, which when combined with water and mechanically agitated generates a foam or lather. Such surfactants are preferred since increased lather is important to consumers as an indication of cleansing effectiveness. In certain personal care embodiments, the surfactants or combinations of surfactants are preferably mild. As used herein, "mild" means that the surfactants as well as to the articles of the present invention demonstrate skin mildness at least milder than common bar soap matrices that typically comprise a combination of natural soap and synthetic surfactant (e.g., Lever 2000® and Zest®). Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H-H_2O$) that passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, to Small et al., issued Jun. 16, 1987. Other testing methodologies for determining surfactant mildness well known to one skilled in the art can also be used.

A wide variety of lathering surfactants are useful herein and include those selected from the group consisting of anionic lathering surfactants, nonionic lathering surfactants, cationic lathering surfactants, amphoteric lathering surfactants, and mixtures thereof.

Anionic Lathering Surfactants

Nonlimiting examples of anionic lathering surfactants useful herein are disclosed in McCutcheon's, *Detergents and Emulsifiers,* North American edition (1986), published by Allured Publishing Corporation; McCutcheon's, *Functional Materials,* North American Edition (1992); and U.S. Pat. No. 3,929,678, to Laughlin et al., issued Dec. 30, 1975.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention. Specific examples of alkyl sulfates that may be used are sodium, ammonium, potassium, magnesium, or TEA salts of lauryl or myristyl sulfate. Examples of alkyl ether sulfates that may be used include ammonium, sodium, magnesium, or TEA laureth-3 sulfate.

Another suitable class of anionic surfactants are the sulfated monoglycerides of the form R1CO—O—CH2—C(OH)H—CH2—O—SO3M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. An example of a sulfated monoglyceride is sodium cocomonoglyceride sulfate.

Other suitable anionic surfactants include olefin sulfonates of the form R1SO3M, wherein R1 is a mono-olefin having from about 12 to about 24 carbon atoms, and M is a water-soluble cation such as ammonium, sodium, potassium, magnesium, triethanolamine, diethanolamine and monoethanolamine. An example of a sulfonated olefin is sodium C14/C16 alpha olefin sulfonate.

Other suitable anionic surfactants are the linear alkylbenzene sulfonates of the form R1-C6H4-SO3M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. An example of this anionic surfactant is sodium dodecylbenzene sulfonate.

Still other anionic surfactants suitable for the compositions of the present invention include the primary or secondary alkane sulfonates of the form R1SO3M, wherein R1 is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. An example of an alkane sulfonate useful herein is alkali metal or ammonium C13–C17 paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates that are based on taurine. Examples of taurates include N-alkyltaurines such as the one prepared by reacting dodecylamine with sodium isethionate as detailed in U.S. Pat. No. 2,658,072.

Another class of suitable anionic surfactants is the acyl isethionates. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form R1—OCH2—C(OH)H—CH2—SO3M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. One example is sodium cocoglyceryl ether sulfonate.

Other suitable anionic surfactants include:
1. sulfonated fatty acids of the form R1—CH(SO4)—COOH and sulfonated methyl esters of the from R1—CH(SO4)—CO—O—CH3, where R1 is a saturated or unsaturated, branched or unbranched alkyl group from about 8 to about 24 carbon atoms (e.g., alpha sulphonated coconut fatty acid and lauryl methyl ester);
2. phosphates such as monoalkyl, dialkyl, and trialkylphosphate salts formed by the reaction of phosphorous pentoxide with monohydric branched or unbranched alcohols having from about 8 to about 24 carbon atoms (e.g., sodium mono or dilaurylphosphate, ethoxylated monoalkyl phosphates, etc.);
3. acyl glutamates corresponding to the formula R1CO—N(COOH)—CH2CH2—CO2M wherein $R^1$ is a saturated or unsaturated, branched or unbranched alkyl or alkenyl group of about 8 to about 24 carbon atoms, and M is a water-soluble cation (e.g., sodium lauroyl glutamate and sodium cocoyl glutamate);
4. alkanoyl sarcosinates corresponding to the formula R1CON(CH3)—CH2CH2—CO2M wherein R1 is a saturated or unsaturated, branched or unbranched alkyl or alkenyl group of about 10 to about 20 carbon atoms, and M is a water-soluble cation (e.g., sodium lauroyl sarcosinate, sodium cocoyl sarcosinate, and ammonium lauroyl sarcosinate);
5. alkyl ether carboxylates corresponding to the formula R1—(OCH2CH2)x-OCH2—CO2M wherein R1 is a saturated or unsaturated, branched or unbranched alkyl or alkenyl group of about 8 to about 24 carbon atoms, x is 1 to 10, and M is a water-soluble cation (e.g., sodium laureth carboxylate);
6. acyl lactylates corresponding to the formula R1CO—[O—CH(CH3)—CO]x-CO2M wherein R1 is a saturated or unsaturated, branched or unbranched alkyl or alkenyl group of about 8 to about 24 carbon atoms, x is 3, and M is a water-soluble cation (e.g., sodium cocoyl lactylate);
7. carboxylates, nonlimiting examples of which include sodium lauroyl carboxylate, sodium cocoyl carboxylate, and ammonium lauroyl carboxylate;
8. anionic flourosurfactants; and
9. natural soaps derived from the saponification of vegetable and/or animal fats & oils exmaples of which include sodium laurate, sodium myristate, palmitate, stearate, tallowate, cocoate.

Any counter cation, M, can be used on the anionic surfactant. Preferably, the counter cation is selected from the group consisting of sodium, potassium, ammonium, monoethanolamine, diethanolamine, and triethanolamine.

Nonionic Lathering Surfactants

Nonlimiting examples of nonionic lathering surfactants that may optionally be included in the compositions of the present invention are disclosed in McCutcheon's, *Detergents and Emulsifiers*, North American edition (1986), published by allured Publishing Corporation; and McCutcheon's, *Functional Materials*, North American Edition (1992).

Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g., C8–30 alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl;

and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809, 060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934.

Other examples of nonionic surfactants include amine oxides. Amine oxides correspond to the general formula $R_1R_2R_3N{\rightarrow}O$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyidiethylamine oxide, di(2-hydroxyethyl) tetradecylamine oxide, 2-dodecoxyethyldimethylamine oxide, 3-dodecoxy-2-hydroxypropyidi(3-hydroxypropyl) amine oxide, dimethylhexadecylamine oxide.

Nonlimiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Cationic Lathering Surfactants

Cationic lathering surfactants can also be optionally included in the compositions of the of the present invention. Suitable cationic lathering surfactants include, but are not limited to, fatty amines, di-fatty quaternary amines, tri-fatty quaternary amines, imidazolinium quaternary amines, and combinations thereof. Suitable fatty amines include monalkyl quaternary amines such as cetyltrimethylammonium bromide. A suitable quaternary amine is dialklamidoethyl hydroxyethylmonium methosulfate.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxy-ethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50® from Henkel), and cocamidopropyl betaine (available as Velvetex BK-35® and BA-35® from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

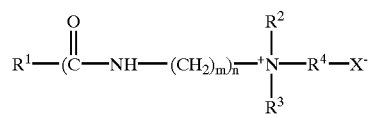

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl Dimethyl Betaine (This Material also has the CTFA Designation Cetyl Betaine)

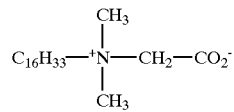

Cocamidopropylbetaine

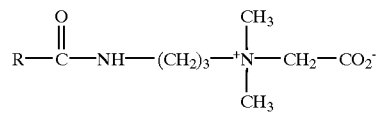

wherein R has from about 9 to about 13 carbon atoms

Cocamidopropyl Hydroxy Sultaine

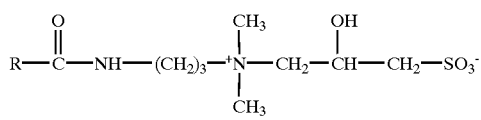

wherein R has from about 9 to about 13 carbon atoms,

Examples of other useful amphoteric surfactants are alkyliminoacetates, and iminodialkanoates and aminoalkanoates of the formulas $RN[(CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091; and the products sold under the trade name "Miranol" and described in U.S. Pat. No. 2,528,378. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants are selected from the group consisting of anionic lathering surfactants selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phosphates, ethoxylated monoalkyl phosphates, sodium cocoglyceryl ether sulfonate, sodium $C_9$–$C_{22}$ soap, and combinations thereof; nonionic lathering surfactants selected from the group consisting of lauramine oxide, cocoamine oxide, decyl polyglucose, lauryl polyglucose, sucrose cocoate, C12–14 glucosamides, sucrose laurate, and combinations thereof; cationic lathering surfactants selected from the group consisting of fatty amines, di-fatty quaternary amines, tri-fatty quaternary amines, imidazolinium quaternary amines, and combinations thereof; amphoteric lathering surfactants selected from the group consisting of disodium lauroamphodiacetate, sodium lauroamphoacetate, cetyl dimethyl betaine, cocoamidopropyl betaine, cocoamidopropyl hydroxy sultaine, and combinations thereof.

Associated Methods

Applicant has found that the compositions of the present invention are useful in a variety of applications directed to enhancement of proteinaceous substrates like skin, hair, nails, and cuticles. The application that is targeted will depend upon the cosmetic benefit agent that is attached to the bonding agent. It is expected, however, that a skilled artisan is capable of envisioning the appropriate cosmetic benefit agent of those disclosed herein that are commensurate with the method of use being disclosed. The methods of use for the compositions disclosed and claimed herein include, but are not limited to: 1) methods of increasing the substantivity of a cosmetic active to skin; 2) methods of moisturizing skin; 3) methods of improving the natural appearance of skin; 4) methods of applying a color cosmetic to skin; 5) methods of deodorizing skin; 6) methods of providing antiperspirant efficacy to skin; 7) methods of preventing, retarding, and/or treating wrinkles; 8) methods of providing UV protection to skin; 9) methods of preventing, retarding, and/or treating cellulite; 10) methods of preventing, retarding, and/or controlling the appearance of oil; and 11) methods of modifying the feel and texture of skin; 12) methods of providing even skin tone; 13) methods of preventing, retarding, and/or treating the appear of spider vessels and varicose veins; 14) methods of masking the appearance of vellus hair on skin; 15) methods of concealing blemishes and/or imperfections in human skin, including acne, age spots, freckles, moles, scars, under eye circles, birth marks, post-inflammatory hyperpigmentation, etc.; 16) methods of preventing, retarding, and/or treating malodor of a mammal; and 17) methods of pre-treating a proteinaceous substrate in preparation for receiving one or more cosmetic benefit agents. Each of the methods discussed herein involve topical application of the claimed compositions on to proteinaceous substrates, particularly skin.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

For each of the bonding agents listed below, m=1 to 100, n=1 to 100, y=1 to 20, z=2 to 500, R=a hydrocarbon chain that optionally contains a heteroatom.

Example 1

Antioxidant-Modified Bonding Agent—Modified Ascorbate

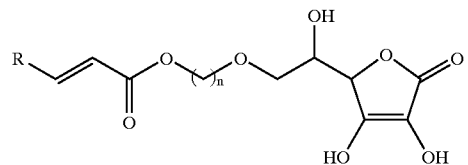

Example 2

Antioxidant-Modified Bonding Agent—Modified Gallate

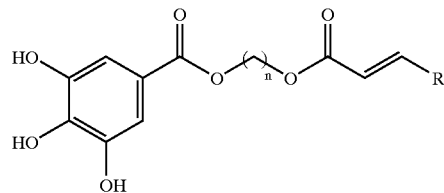

Example 3
Colorant-Modified Bonding Agent—Modified F&DC Yellow 6

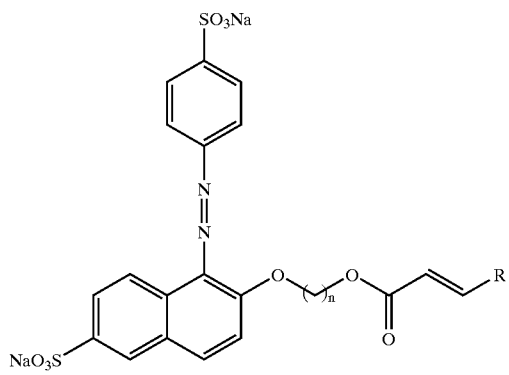

Example 4
Colorant-Modified Bonding Agent—Modified D&C Red 36

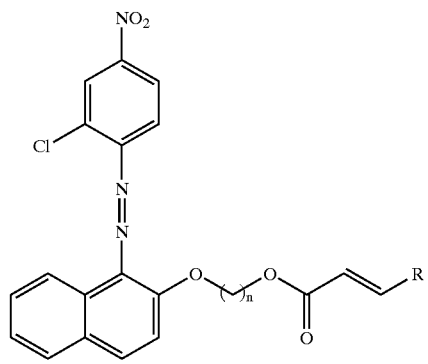

Example 5
Colorant-Modified Bonding Agent—Modified D&C Green 8

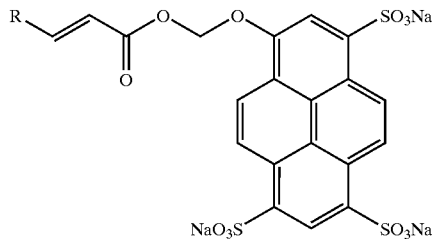

Example 6
Humectant-Modified Bonding Agent—Modified Glycerol

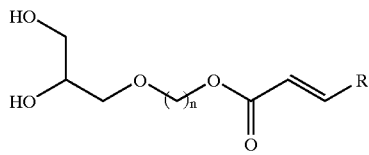

Example 7
Humectant-Modified Bonding Agent—Modified PEG

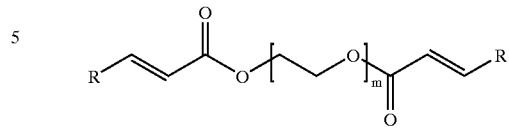

Example 8
Silicone-Modified Bonding Agent

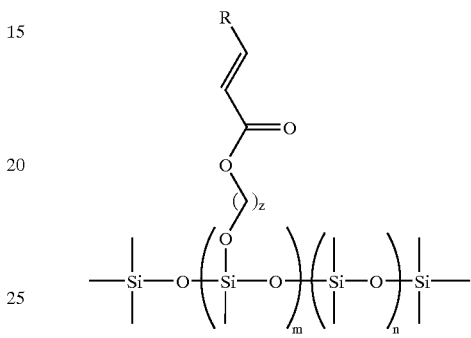

Example 9
Silicone-Modified Bonding Agent

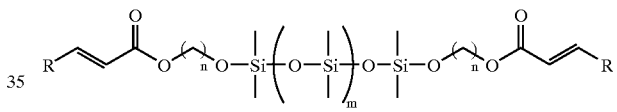

Example 10
Sunscreen-Modified Bonding Agent—Modified Benzophenone-3

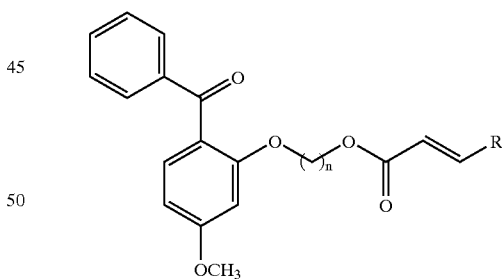

Example 11
Sunscreen-Modified Bonding Agent—Modified Octyl Methoxycinnamate

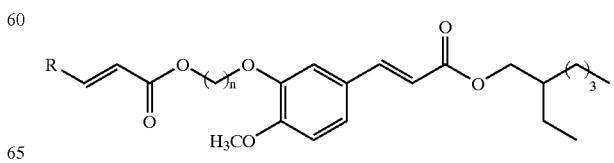

Example 12

A lipstick product is prepared by mixing the following ingredients as detailed below.

| Ingredient | Wt % |
| --- | --- |
| Polybutene | 4.536 |
| Lanolin Oil | 18.342 |
| Octoxyglyceryl Behenate | 18.342 |
| Stearyl heptanoate | 8.856 |
| Jojoba oil | 8.856 |
| Castor oil | 21.78 |
| Butylated hydroxytoluene | 0.054 |
| Butylated hydroxyanisole | 0.054 |
| Microcrystalline Wax | 6.84 |
| Polyethylene 500 | 6.84 |
| Modified D&C Red 36 (from Example 4) (Amphiphlic lipid phase) | 4.5 |
| Lecithin | 0.475 |
| Cholesterol | 0.475 |
| dicetyl phosphate | 0.05 |

Recrystallize modified D&C Red 36 using the single solvent method. Mill modified D&C Red 36 with Castor oil until desired Particle size is reached. Mixing of the different compounds is performed at a temperature between 100–120 C. with stirring until fully homogenous. Heat amphiphilic lipid phase to 100 C. under nitrogen, add phases together, mill until uniform, mold, and cool.

Example 13

A foundation compact product is prepared by mixing the following ingredients as indicated below.

| Phase | Ingredient | Wt % |
| --- | --- | --- |
| A | TiO2 silicone treated | 5.25 |
| A | Hydrophobic Yellow Iron Oxide Slurry (55% Pigment, 16.15% Cyclomethicone, 28.85% Dimethicone Copolyol) | 0.80 |
| A | Hydrophobic Red Iron Oxide Slurry (70% pigment, 10.7% cyclomethicone, 19.3% Dimethicone Copolyol) | 0.31 |
| A | Hydrophobic Black Iron Oxide Slurry (65% pigment, 13.2% cyclomethicone, 21.8% Dimethicone Copolyol) | 0.12 |
| A | Hydrophobic Talc | 2.36 |
| A | TiO2 -MT100T (micronized) | 0.16 |
| A | DC245 (cyclomethicone) | 74.96 |
| A | DC5225C (dimethicone copolyol - 10% active) | 0.31 |
| B | Silicone Elastomer | 2.40 |
| B | propylparaben (preservative) | 0.00 |
| B | Modified Glycerol (from Example 6) | 7.08 |
| C | Ozokerite Wax | 6.25 |

The pigment slurries are created by combining the pigment, wetting agent (cyclomethicone), and dispersant (copolyol) and milling to the desired particle size. Ingredients in phase A are added together and high shear milled until the desired particle size. Phase B ingredients are added to phase A ingredients and mixed until uniform. The mixture of phase A &B is heated while mixing to 85–90 C. Phase C is added and mixed until completely melted and the mixture is uniform. The mixture is then poured into a mold.

Example 14

A lip gel product is prepared by combining the following ingredients as detailed below.

| Ingredient | Wt % |
| --- | --- |
| Silicone elastomer | 4.0 |
| cyclomethicone | 83.0 |
| Dimethicone Fluid | 4.5 |
| Modified D&C Green 8 (from Example 5) | 6 |
| Modified FD&C Yellow 6 (from Example 3) | 2.5 |

All Ingredients are mixed together using low to medium shear.

Example 15

A lip balm product is prepared by combining the following ingredients as detailed below.

| Phase | Ingredient | Wt % |
| --- | --- | --- |
| A | Petrolatum | 10.0 |
| A | Modified Glycerol (from Example 6) | 10.0 |
| A | Silicone elastomer | 3.4 |
| A | cyclomethicone | 64.3 |
| A | Dimethicone copolyol | 5.0 |
| A | Preservative | 0.3 |
| B | Ozokerite wax | 7.0 |

Ingredients in phase A are added together and mixed using low shear until uniform. Phase A is heated to 85–90 C. while mixing. Phase B is added and mixed until uniform. This mixture is then poured into a mold.

Example 16

A moisturizing lotion is prepared by mixing the ingredients as detailed below.

| | Ingredient | Wt % |
| --- | --- | --- |
| Main Water Phase | | |
| | USP Water | 63.77435 |
| | Disodium EDTA | 0.100 |
| | Arlatone 2121 | 1.00 |
| Part D - Particulate Premix | | |
| (D) | USP Water | 5.000 |
| (D) | Glycerine | 6.930 |
| (D) | Kobo Titanium Dioxide | 0.544 |
| Part A - Neutralization Premix | | |
| (A) | USP Water | 3.013 |
| (A) | Sodium Hydroxide | 0.0125 |
| Part B - Niacinamide Premix | | |
| (B) | USP Water | 5.000 |
| (B) | Panthenol | 0.500 |
| (B) | Modified Ascorbate (from Example 1) | 2.000 |
| (B) | FD&C Yellow No. 5 | 0.00115 |
| (B) | FD&C Red No. 40 | 0.00050 |
| (C) | Sefa Cottonate | 0.670 |
| (C) | Isopropyl Isostearate | 1.330 |

| Ingredient | | Wt % |
|---|---|---|
| (C) | Tocopherol Acetate | 0.500 |
| (C) | Permethyl 101A | 3.000 |
| (C) | Cetyl Alcohol CO-1695 | 0.720 |
| (C) | Adol 62 | 0.480 |
| (C) | Nipigin A | 0.200 |
| (C) | Ueno Propylparaben NF | 0.100 |
| (C) | Emersol 132 | 0.100 |
| (C) | Myrj 59 | 0.100 |
| Part E | | |
| (E) | Sepigel | 2.500 |
| | Q2-1403 | 2.000 |
| | Benzyl Alcohol | 0.250 |
| | Fiery 5 | 0.175 |

In an appropriate container, prepare the Neutralization Premix. Add part A ingredients to container and mix with a stir bar until homogenous. In an appropriate container prepare Part D (Particulate Premix). Mix by mixer until homogenous. In an appropriate container, prepare the modified ascorbate premix. Add Part B ingredients into container, except FD&C Yellow/Red. Heat to no higher than 40° C. while mixing until modified ascorbate is dissolved. Add FD&C Yellow/Red. Mix until dissolved. Prepare the Oil Phase. Add part C ingredients to oil phase except Permethyl 101A and begin heating to 70–80° C. while mixing Maintain Temperature once heated. Prepare the water phase. Add USP water to appropriate pyrex beaker, and begin heating to 70–80 C. while mixing with a prop blade at 250–500 rpm. When water phase is between 70–80° C. add Disodium EDTA and Arlatone 2121 to beaker and allow to dissolve. Mix at least 5 minutes. When Oil & Water phases are between 70–80° C. begin to mill water phase. Slowly add oil phase to water phase while milling. Mill for 2–3 min. Add Particulate premix(part D) slowly, by hand pouring. Add neutralization premix (part A) slowly. Cool batch to 60° C. and add sepigel. Switch to U-blade once formula looks smooth. Cool batch to 50° C., then add modified ascorbate premix, Benzyl alcohol and Q2-1402. Cool batch to 40° C. with periodic spatula mixing to insure homogeneity. When temperature reaches 40° C., add fragrance. Mill for 2–3 minutes.

Example 17

A solid antiperspirant stick of the present invention is prepared as follows:

| Ingredient | Wt % |
|---|---|
| Modified Gallate (from Example 2) | 8.0 |
| Stearyl Alcohol | 10.0 |
| Hydrogenated Castor Oil-mp 86 degrees C. | 4.0 |
| Aluminum Chlorohydroxide | 40.0 |
| Isopar "V"[1] | 37.0 |
| Fragrance | 1.0 |

[1](Isopar "V" Avg. Mol. Wt. 197 B.P. Range, 255–301 degrees C.)

In a suitable vessel, neat, chemically synthesized modified ascorbate is dissolved using an appropriate solvent. The modified asdcorbate is then recrystallized by sublimation method. Next, the recrystallized modified ascorbate is milled to the appropriate particle size.

In separate vessel containing a heat source, the isoparaffin liquids, the water-insoluble liquid emollients, the surface active agent, and the water-insoluble waxes are heated to a temperature sufficient to form a solution of these materials. Next, the aluminum chlorohydroxide is added with gentle agitation, followed by the recrystallized modified ascorbate and remaining ingredients. The solution is mixed until a homogenous suspension is formed. The suspension is cooled to a temperature above the solidification point and is then poured into suitable containers. An antiperspirant composition, comprised as above, is applied to the underarm area of a human subject, and reduces the perspiration in the applied area.

Example 18

A long wearing eye shadow is prepared including the following ingredients that are mixed as detailed below.

| Ingredient | Wt % |
|---|---|
| Pearl Mica CF | 4.41 |
| Glycerol Ester of Tall Oil Rosin | 3.00 |
| GE SFE 839 Cross-linked Siloxane Elastomer gel[1] | 44.6 |
| Polyethylene AC-617A | 5.46 |
| Beeswax White, Flakes | 3.00 |
| Propylparaben, NF | 0.10 |
| Tenox BHA | 0.20 |
| Bentone 38 CF or Type | 5.40 |
| Propylene Carbonate | 1.00 |
| Phenoxyethanol | 0.80 |
| Modified D&C Green 8 (from Example 5) | 0.18 |
| Talc 2755 | 3.00 |
| Magnesium Carbonate 309 | 2.00 |
| Glyceryl Tribehenate | 2.00 |
| Paraffin Wax | 1.50 |
| Modified Silicone (from one of Examples 8 or 9) | 1.30 |
| Vanillin | 0.01 |
| Lecithin, Liquid | 0.54 |
| Aluminum Starch Octenyl Succinate | 5.00 |
| Pigment | 16.5 |

[1]5% Dimethicone/vinyl dimethicone cross-polymer in cyclomethicone.

Example 19

A long wearing sunscreen product is prepared as detailed below.

| Ingredient | Wt % |
|---|---|
| Water | QS100 |
| Glycerine | 3.00 |
| Disodium EDTA | 0.10 |
| Methyl Paraben | 0.25 |
| Sepigel 305 | 2.00 |
| Octyl Salicylate | 5.00 |
| Modified Benzophenone-3 (from Example 10) | 2.00 |
| Modified octyl methoxycinnamate (from Example 11) | 1.50 |
| Isohexadecane | 2.00 |
| Steareth-21 | 0.80 |
| Stearetch-2 | 0.10 |
| Cetyl alcohol | 0.80 |
| Stearyl Alcohol | 0.80 |
| Behenyl Alcohol | 0.80 |
| Propyl Paraben | 0.15 |

Prepare a water phase by combining the water, glycerin, disodium EDTA, methyl paraben in an appropriate vessel with mixing and heating to approximately 75° C. Prepare the oil phase by combining the modified benzophenone-3, octyl methoxycinnamate, isohexadecane, cetyl alcohol, stearyl alcohol, propyl paraben, octyl salicyclate, steareth-21, steareth-2, and behenyl alcohol into a separate vessel with mixing and heating to approximately 75° C. Mix the oil phase into the water phase with shearing to form an emulsion. Cool the emulsion to 60° C. with shearing and add Sepigel 305. Slowly stir the emulsion and cool to approximately 30° C., and package as desired.

Example 20

A long wearing sunscreen product is made as detailed below.

| Ingredient | Wt % |
| --- | --- |
| Water | QS100 |
| Glycerine | 2.00 |
| Disodium EDTA | 0.10 |
| Methy Paraban | 0.25 |
| Sepigel 305 | 2.50 |
| 2-Phenyl-Benzimidazole 5-Sulphonic Acid | 1.00 |
| Triethanolamine | 0.50 |
| Octyl Salicylate | 3.00 |
| Modified Benzophenone-3 (from example 10) | 2.00 |
| 2-ethylhexyl-p-methoxycinnamate | 1.33 |
| Isohexadecane | 2.00 |
| Cetyl alcohol | 0.70 |
| Stearyl Alcohol | 0.70 |
| Propyl Paraben | 0.15 |
| Modified PEG-100 (from Example 7) | 0.10 |

Prepare a water phase by combining the water, glycerin, disodium EDTA, methyl paraben in an appropriate vessel with mixing and heating to approximately 75° C. Prepare the oil phase by combining the modified benzophenone-3,2-ethylhexyl-p-methoxycinnamate, isohexadecane, cetyl alcohol, stearyl alcohol, propyl paraben, octyl salicylate, and modified PEG-100 into a separate vessel with mixing and heating to approximately 75° C. Mix the oil phase into the water phase with shearing to form an emulsion. Cool the emulsion to 60° C. with shearing and add Sepigel 305, 2-phenyl-benzimidazole-5-sulphonic acid, and triethanolamine. Slowly stir the emulsion and cool to approximately 30° C., and package as desired.

What is claimed is:

1. A cosmetic composition comprising:
   a) a safe and effective amount of a bonding agent comprising the structure

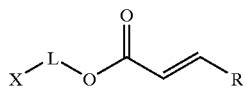

wherein
   X represents a cosmetic benefit agent;
   L represents an optional chemical linker; and
   R represents a hydrocarbon chain that optionally contains heteroatoms; and
   b) a cosmetically acceptable carrier for the bonding agent wherein the composition is administered topically to a mammalian proteinaceous substrate and wherein the bonding agent reacts with a protein contained in the substrate such that the bonding agent is covalently attached to the substrate.

2. The composition of claim 1 wherein the composition comprises from about 0.001% to about 25%, by weight of the composition, of the bonding agent.

3. The composition of claim 1 wherein X is selected from the group consisting of absorbents, anti-acne actives, anti-caking agents, anti-cellulite agents, anti-foaming agents, anti-fungal actives, anti-inflammatory actives, anti-microbial actives, anti-oxidants, antiperspirant/deodorant actives, anti-skin atrophy actives, anti-viral agents, anti-wrinkle actives, artificial tanning agents and accelerators, astringents, barrier repair agents, binders, buffering agents, bulking agents, chelating agents, colorants, dyes, enzymes, essential oils, film formers, flavors, fragrances, humectants, hydrocolloids, light diffusers, nail enamels, opacifying agents, optical brighteners, optical modifiers, particulates, perfumes, pH adjusters, sequestering agents, skin conditioners/moisturizers, skin feel modifiers, skin protectants, skin sensates, skin treating agents, skin exfoliating agents, skin lightening agents, skin soothing and/or healing agents, skin thickeners, sunscreen actives, topical anesthetics, vitamin compounds, and combinations thereof.

4. The composition of claim 1 wherein said composition is a cosmetic product selected from the group consisting of skin moisturizers, lipsticks, nail polishes, foundations, mascaras, rouges, lip pencils, eyeliners, concealers, and combinations thereof.

5. A method of increasing the substantivity of a cosmetic active to skin wherein said method comprises topically applying the composition of claim 1 to skin.

6. A method of moisturizing skin wherein the method comprises topically applying the skin moisturizer of claim 4 to skin.

7. A method of improving the natural appearance of skin wherein said method comprises topically applying the composition of claim 1 to skin.

8. A method of applying a color cosmetic to skin wherein said method comprises topically applying the composition of claim 1 to skin wherein X is a colorant.

9. A method of deodorizing skin wherein said method comprises topically applying the composition of claim 1 to skin wherein X is a deodorant active.

10. A method of providing antiperspirant efficacy to skin wherein said method comprises topically applying the composition of claim 1 to skin wherein X is an antiperspirant active.

11. A method of preventing, retarding, and/or treating wrinkles wherein said method comprises topically applying the composition of claim 1 to skin wherein X is an anti-wrinkle active.

12. A method preventing, retarding, and/or treating cellulite wherein said method comprises topically applying the composition of claim 1 to skin wherein X is an anti-celllulite agent.

13. A method of regulating the condition of mammalian skin wherein said method comprises topically applying the composition of claim 1 wherein X is selected from the group consisting of phytantriol, farnesol, bisabolol, vitamin B3 compounds, pentapeptides, and combinations thereof.

14. The composition of claim 1 wherein L comprises one or more hydrocarbon chains containing heteroatoms.

15. The composition of claim 14 wherein said heteroatoms are selected from the group consisting of S, N, Se, O, substituted or unsubstituted aryls, Si, SiO, siloxane "D" groups [{(CH$_3$)}—Si—O$_3$], siloxane "M" groups [{(CH$_3$)$_3$}—Si—O], and siloxane "T" groups [{(CH$_3$)}—Si—O$_{3/2}$], and combinations thereof.

* * * * *